(12) United States Patent
Pruneri et al.

(10) Patent No.: US 12,282,151 B2
(45) Date of Patent: Apr. 22, 2025

(54) OPTICAL ENDOSCOPE

(71) Applicants: FUNDACIÓ INSTITUT DE CIÈNCIES FOTÒNIQUES, Castelldefels (ES); INSTITUCIÓ CATALANA DE RECERCA I ESTUDIS AVANÇATS, Barcelona (ES)

(72) Inventors: Valerio Pruneri, Castelldefels (ES); Robin Camphausen, Castelldefels (ES)

(*) Notice: Subject to any disclaimer, the term of this patent is extended or adjusted under 35 U.S.C. 154(b) by 669 days.

(21) Appl. No.: 16/768,566

(22) PCT Filed: Nov. 30, 2017

(86) PCT No.: PCT/ES2017/070787
§ 371 (c)(1),
(2) Date: May 29, 2020

(87) PCT Pub. No.: WO2019/106209
PCT Pub. Date: Jun. 6, 2019

(65) Prior Publication Data
US 2020/0310103 A1    Oct. 1, 2020

(51) Int. Cl.
*G02B 6/26* (2006.01)
*A61B 1/00* (2006.01)
*A61B 1/07* (2006.01)
*G02B 23/26* (2006.01)

(52) U.S. Cl.
CPC ............ *G02B 23/26* (2013.01); *A61B 1/0011* (2013.01); *A61B 1/00195* (2013.01); *A61B 1/07* (2013.01); *G02B 6/26* (2013.01)

(58) Field of Classification Search
CPC .................................. A61B 1/07; G02B 6/26

USPC ........................................................... 385/33
See application file for complete search history.

(56) References Cited

U.S. PATENT DOCUMENTS

| 4,366,565 A | * | 12/1982 | Herskowitz | G02B 6/4206 398/59 |
| 7,349,589 B2 | * | 3/2008 | Temelkuran | G02B 6/02385 385/11 |
| 8,548,286 B2 | * | 10/2013 | Zheng | G02B 6/12004 385/24 |

(Continued)

FOREIGN PATENT DOCUMENTS

| BR | 112014019282 B1 | * | 12/2022 |
| CN | 103930816 A | | 7/2014 |

(Continued)

OTHER PUBLICATIONS

Fleming, Christine, et al., "Optical Coherence Tomography Imaging of Cardiac Radiofrequency Ablation Lesions," Poster presented at Biomedical Optics 2008, St. Petersburg, Florida, Mar. 16-19, 2008; 7 pages.

(Continued)

*Primary Examiner* — Kaveh C Kianni
(74) *Attorney, Agent, or Firm* — Sterne, Kessler, Goldstein & Fox P.L.L.C.

(57) ABSTRACT

The invention relates to an optical endoscope (1) comprising an optical fiber element (2) with a proximal end (3) and a distal end (4), wherein an optical waveguide block (6) is arranged at the distal end (4) of the optical fiber element (2), the optical waveguide block (6) comprising a rigid material with two or more optical waveguides (7) formed therein.

17 Claims, 6 Drawing Sheets

(56) References Cited

U.S. PATENT DOCUMENTS

| | | | |
|---|---|---|---|
| 9,661,986 B2 | 5/2017 | Shahmoon et al. | |
| 10,082,425 B2* | 9/2018 | Gastaldo | G01J 3/0208 |
| 10,254,536 B2* | 4/2019 | Yeoh | G02B 6/0028 |
| 10,338,391 B2* | 7/2019 | Yeoh | G02B 6/0076 |
| 10,429,580 B2* | 10/2019 | Zalevsky | G02B 6/262 |
| 11,051,698 B2 | 7/2021 | Hendriks et al. | |
| 2001/0031942 A1 | 10/2001 | Tollner et al. | |
| 2003/0208252 A1 | 11/2003 | O'Boyle et al. | |
| 2004/0204651 A1* | 10/2004 | Freeman | A61B 5/0075 600/478 |
| 2005/0084200 A1* | 4/2005 | Meis | G02B 6/3608 385/14 |
| 2007/0041083 A1* | 2/2007 | Di Teodoro | C03B 37/10 359/333 |
| 2007/0076212 A1 | 4/2007 | Zuluaga | |
| 2007/0086712 A1* | 4/2007 | Shani | G02B 6/065 385/101 |
| 2008/0089641 A1 | 4/2008 | Feldchtein | |
| 2009/0018393 A1 | 1/2009 | Dick et al. | |
| 2009/0306520 A1 | 12/2009 | Schmitt et al. | |
| 2010/0041986 A1 | 2/2010 | Nguyen et al. | |
| 2010/0046953 A1 | 2/2010 | Shaw et al. | |
| 2012/0224802 A1* | 9/2012 | Zheng | B41J 2/465 385/14 |
| 2014/0055562 A1* | 2/2014 | Demers | H04N 23/56 348/45 |
| 2014/0058197 A1 | 2/2014 | Salahieh et al. | |
| 2015/0178939 A1* | 6/2015 | Bradski | H04N 13/00 345/633 |
| 2015/0268415 A1* | 9/2015 | Schowengerdt | G02F 1/335 385/119 |
| 2016/0051321 A1 | 2/2016 | Salahieh et al. | |
| 2016/0143517 A1* | 5/2016 | Vance | A61B 1/00096 600/177 |
| 2016/0357007 A1 | 12/2016 | Swanson | |
| 2019/0170945 A1* | 6/2019 | Fortusini | G02B 6/13 |

FOREIGN PATENT DOCUMENTS

| | | | |
|---|---|---|---|
| CN | 106999030 A | 8/2017 | |
| EP | 0 211 976 | 3/1987 | |
| JP | H0681506 U | 11/1994 | |
| JP | H08-179131 A | 7/1996 | |
| JP | 2003-167203 A | 6/2003 | |
| JP | 4688248 B2 * | 5/2011 | G02B 6/12002 |
| JP | 2016-007336 A | 1/2016 | |
| TW | 201802433 A * | 1/2018 | G01B 11/022 |
| WO | 2017016663 A1 | 2/2017 | |
| WO | WO-2018022319 A1 * | 2/2018 | G02B 6/13 |

OTHER PUBLICATIONS

Fleming, Christine, et al., "Real-Time Imaging of Radiofrequency Cardiac Ablation Using Optical Coherence Tomography," OSA Technical Digest (CD) (Optical Society of America, Mar. 2008), paper BMD88, Mar. 2008; 3 pages.

Boppart, Stephen A., et al., "Real-Time Optical Coherence Tomography for Minimally Invasive Imaging of Prostrate Ablation," Computer Aided Surgery 6:94-103, Accepted Feb. 2001, published online Jan. 2010; 10 pages.

Patel, Nirlep A., et al., "Guidance of Aortic Ablation Using Optical Coherence Tomography," The International Journal of Cardiovascular Imaging 19:171-178, Apr. 2003; 8 pages.

De Boer, Johannes F., et al., "Two-Dimensional Birefringence Imaging in Biological Tissue Using Polarization Sensitive Optical Coherence Tomography," SPIE vol. 3196, 0277, pp. 32-37, Jan. 1998; 6 pages.

Everett, M.J., et al., "Birefringence Characterization of Biological Tissue By Use of Optical Coherence Tomography," Optics Letters, vol. 23, No. 3, Feb. 1, 1998; 3 pages.

Fleming, Christine, "Characterization of Cardiac Tissue Using Optical Coherence Tomography," Department of Biomedical Engineering, Case Western Reserve University, May 2010; 210 pages.

International Search Report and Written Opinion directed to related International Patent Application No. PCT/ES2017/070787 mailed Jul. 30, 2018; 12 pages.

Davis K M et al.: "Writing waveguides in glass with a femtosecond laser", Optics Letters, Optical Society of America, US, vol. 21, No. 21; Nov. 1996 (Nov. 1, 1996), pp. 1729-1731.

* cited by examiner

OPTICAL ENDOSCOPE

BACKGROUND

The invention relates to an optical endoscope comprising an optical fiber element with a proximal end and a distal end.

Optical endoscopes are instruments for looking inside a volume through a small opening. Endoscopes are typically used in medicine to look inside the human body. However, the use of endoscopes is not restricted to medicine. Endoscopes are also used for visual inspection of work-pieces such as engines, turbines or the like. Endoscopes for such a technical use are sometimes referred to as "borescope". The term "endoscope" as used herein shall refer to both medical and non-medical use.

An endoscope usually comprises a flexible optics that guides the light between the so-called "distal end" inside the object to be examined to the so called "proximal end" outside of the object. Usually, but not always, there is some miniaturized scanning and/or imaging apparatus at the distal end, while more elaborate optics, whose purpose includes magnifying the transmitted image onto a digital image sensor or an eyepiece, are found at the proximal end. Most commonly, endoscopes obtain a scattering image, however fluorescence imaging and optical coherence tomography are widely used too.

For the flexible optics, usually optical fibers are used. Among the possible fiber types fiber bundles as well as multi-mode fibers can be used. Multi-core fibers have also been commonly used.

An important limitation that is connected with the use of optical fibers is the low numerical aperture of the fibers that results in a small acceptance angle and thus a small field of view.

One approach known from WO 2017/016663 A1 uses an endoscope with a flexible tubular sheath containing optical fibers. A distal tip with multiple optical ports spread in three-dimensions including flexible waveguides is described. These waveguides either continue into the body of the endoscope through the same number of fibers or are coupled to a multiplexer which connects to a few or a single optical fiber continuing through to the endoscope's proximal end.

The technology to produce the endoscope with a corresponding distal tip is cumbersome and costly. Moreover, the flexible waveguides connecting the optical ports to the proximal end or to the multiplexer have a high possibility of breakage during fabrication (as they have to be subjected to strong bending) or during use of the latter if a proper package is not employed. In addition, when a multiplexer is used, including a cascade of couplers and splitters, significant signal loss occurs. For many applications, such additional optical loss is detrimental, if not completely preventing the functionality of the device. The scheme is also difficult to adapt to different fiber geometries, for example to different multi-core fiber geometries.

It is therefore an object of the present invention to provide an improved optical endoscope, which is mechanically more reliable and adaptable in use.

This object is achieved with an optical endoscope according to claim 1. Preferred embodiments are specified in the dependent claims.

SUMMARY

According to the invention, an optical waveguide block is arranged at the distal end of the optical fiber element, wherein the optical waveguide block comprises a rigid material in which two or more optical waveguides are formed. Since the two or more optical waveguides are formed in a rigid material, the invention allows for long-term stability and a higher mechanical reliability as compared to known solutions using flexible waveguides.

As mentioned above, the use of the optical endoscope is not particularly limited. The endoscope may be an endoscope for medical purposes or for non-medical purposes. At the proximal end, imaging optics and/or an image sensor and/or an eyepiece may be provided. The imaging optics may include elements for magnifying the transmitted image onto the digital image sensor or the eyepiece.

The optical fiber element may be flexible. However, the optical fiber element may also be rigid.

The optical fiber element may particularly comprise one or more optical fibers, particularly in a common flexible jacket. The common flexible jacket may be made of a plastic material, particularly an elastomer.

The optical waveguide block may be a massive or solid element (not hollow). In other words, the optical waveguide block may not comprise a cavity in which the optical waveguides are provided. Instead, the two or more optical waveguides may be embedded separately in the rigid material of the optical waveguide block.

The optical waveguide block may be rigidly coupled to the distal end of the optical fiber element. Thus, the optical waveguide block may be fixed or immovable with respect to the distal end of the optical fiber element. The optical waveguide block may be coupled or affixed to the distal end of the optical fiber element either via a mechanical, an adhesive (chemical) and/or a fusion (thermal) fixing.

The optical waveguide block may be coupled to the distal end of the optical fiber element such that light may be transmitted via the two or more optical waveguides and the optical fiber element to the proximal end of the endoscope. For instance, a butt coupling may be realized.

The number of optical waveguides in the optical waveguide block is not particularly limited. The actual number depends on the intended application. For many applications, four or more optical waveguides may be used.

The two or more optical waveguides may be arbitrarily arranged within the optical waveguide block, particularly depending on the desired application. The optical waveguides may particularly be arranged in a three-dimensional (3-D), non-intersecting manner. The optical waveguides may also extend in two dimensions (2-D). One or more of the optical waveguides may be curved. One or more of the optical waveguides may be straight or uncurved. If both ends of all the waveguides are arranged in a common plane, the optical waveguides are considered to be arranged in a 2-D distribution, otherwise in a 3-D distribution.

The two or more optical waveguides may be single-mode or multi-mode waveguides. It is possible to vary from a single-mode to a multi-mode waveguide by increasing the cross section and/or the refractive index contrast of the waveguide. The refractive index contrast corresponds to the difference in the refractive index between the waveguide and its surrounding medium (cladding).

The two or more optical waveguides may be integrally formed with the rigid material of the optical waveguide block. In other words, the two or more optical waveguides may be formed by the rigid material itself. In this way, no separate elements need to be introduced into the optical wave guide block which yields a simplified structure with high mechanical reliability.

The two or more optical waveguides may particularly be formed by parts of the rigid material having a higher refractive index than the surrounding parts. The optical waveguides, thus, may be formed by a positive refractive index change in the rigid material. The surrounding parts of the rigid material may form the cladding of the optical waveguides.

The two or more optical waveguides may particularly be obtained by ultrafast laser inscription through the volume of the optical waveguide block. The ultrafast laser inscription is preferably performed with laser pulses of duration lower than 1 ps.

A filter or other optical element may be formed in the optical waveguide block, particularly obtained by ultrafast laser inscription. For instance, one or more FBG (Fiber Bragg Grating) filters may be formed in the optical waveguide block, particularly in one or more of the optical waveguides.

The rigid material is optically transparent at the operating wavelength of the optical endoscope. It may also be optically transparent for the laser used for ultrafast laser inscription. The operating wavelength of the optical endoscope may be below 2 µm, particularly below 1.6 µm, for instance between 1.3 µm and 1.55 µm.

The optical waveguide block may consist of the rigid material. The rigid material may particularly comprise or consist of a glass, a polymer and/or a semiconductor. Examples of materials are silicate and/or multi-component glasses, perfluorinated polymer, silicon and silicon nitride.

Each of the two or more optical waveguides may comprise one end facing the optical fiber element and arranged in a first surface of the optical waveguide block, the so-called coupling end, and one end facing away from the optical fiber element and arranged in a second surface of the optical waveguide block, the so-called object end. The object end may particularly face the object when the endoscope is in use. The two or more optical waveguides may particularly form tubes or channels connecting the coupling end and the object end. Geometrically, thus, the two or more optical waveguides resemble optical fibers. The cladding may be provided by the rigid material surrounding the optical waveguides, as mentioned above.

The optical fiber element may comprise a multi-core optical fiber, wherein the two or more optical waveguides are coupled to the optical fiber element such that at the coupling end the two or more optical waveguides line up with the cores of the multi-core optical fiber. In other words, a butt coupling of the cores of the multi-core fiber with the optical waveguides in the optical waveguide block can be realized. The waveguide block can be index matched to the optical fiber element. In this way, it is possible to reduce optical loss.

The individual cores of the multi-core optical fiber may be single mode cores at the operating wavelength. Single mode waveguides are compatible with coherent imaging techniques such as optical coherence tomography.

Additionally or alternatively, the optical fiber element may comprise a multi-mode optical fiber, wherein the two or more optical waveguides are coupled to the multimode optical fiber via a photonic lantern section formed in the rigid material of the optical waveguide block. In this way, it is possible to omit the multiplexing section as used in the prior art.

A photonic lantern corresponds to an optical element connecting a multi-mode waveguide to multiple waveguides with fewer modes, particularly single mode.

The geometry of the optical waveguide block is not particularly limited. Also the geometry of the optical waveguides within the rigid material is not particularly limited. Both may depend on the desired application.

The optical waveguide block may be rotationally symmetric, for instance cylindrical or in the form of a truncated cone. The optical waveguide block may also have the form of two or more rotationally symmetric elements joined to each other, for instance, a circular cylinder and a hemisphere.

The optical waveguide block may comprise or consist of one or more planar chips. Each planar chip can comprise one or more of the optical waveguides. The waveguides may be curved. Each planar chip may also comprise multiplexers and/or splitters formed therein, particularly by ultrafast laser inscription. As used herein, a "planar chip" refers to a geometrical form whose extension in one direction (thickness) is significantly less (at least three times less) than the extension in the other two directions (length, width). In its simplest form, a planar chip may be a rectangular plate. More than one planar chip may be connected to each other thereby forming a more complex geometry for the optical waveguide block. For instance, two planar chips may be arranged orthogonal to each other, particularly such that each of the planar chips is divided in half by the other of the two planar chips.

The coupling end may be a polished, flat surface perpendicular to the longitudinal axis of the optical fiber element.

The object end may be a flat surface perpendicular to or inclined with regard to the longitudinal axis of the optical fiber element. By using an inclined surface, back reflections may be minimized or removed.

The two or more optical waveguides may particularly fan out from the coupling end to the object end such that the inter-core spacing at the object end is larger than at the coupling end. In this case, it is possible to expand the field of view of the endoscope without changing the solid angle.

The object end may be polished flat.

The object end may be curved; particularly the object end may be hemispherical. In this way, it is possible to map a flat 2-D distribution of waveguide ends present at the coupling end to a 3-D hemisphere. In this way, it is possible to expand the solid angle and consequently also the field of view.

The object end may be curved continuously or discontinuously. The object end may also be composed of a plurality of polished flat facets, joined together to form a curved, particularly hemispherical, surface.

The mapping of the spatial distribution of the ends of the two or more optical waveguides at the coupling end to the spatial distribution of the ends of the two or more optical waveguides at the object end may be mirror symmetrical with regard to a plane extending parallel to the longitudinal axis of the optical fiber element. In other words, optical waveguides in the optical waveguide block may intersect a plane extending parallel to the longitudinal axis when extending from the coupling end to the object end. In this way, a larger radius of curvature for the optical waveguides can be realized, reducing curvature losses. Optical waveguides extending from the two sides of the plane may intersect the plane at different positions, thereby avoiding intersecting waveguides. Also inter-waveguide coupling can be kept acceptably low in this way.

The plane extending parallel to the longitudinal axis may include a symmetry axis of the optical fiber element and, thus, may correspond to a symmetry plane of the optical fiber element. The plane may also form a symmetry plane of the optical waveguide block coupled to the optical fiber element. If the optical waveguide block is rotationally symmetric, the plane may also include the rotational axis of symmetry of the optical waveguide block. As mentioned above, the plane may also form a symmetry plane for the distribution of the optical waveguides in the optical waveguide block. Instead of the symmetry plane, the symmetry axis of the optical fiber element or of the optical waveguide block may be used as reference for some embodiments.

Additional optics, particularly one or more GRIN (graded-index) lenses and/or one or more micro lenses, may be coupled with the optical waveguide block. The additional optical elements may be used for focusing light, for instance.

A separate micro lens may be coupled to each end of the optical waveguides at the object end of the optical waveguide block, for instance.

The one or more micro lenses may be made from fused silica, silicon or any other material transparent at the operating wavelength of the endoscope. The one or more micro lenses may particularly be plano-convex lenses.

Optical waveguides in the optical waveguide block may be arranged such that waveguides having ends at the coupling end with a radial distance less than a predefined distance to the longitudinal axis of the optical fiber element are curved towards a lateral part of the object end, while waveguides having ends at the coupling end with a radial distance to the longitudinal axis of the optical fiber element larger than the predefined distance continue to a forward facing part of the object end. This configuration again allows reducing curvature loss since small curvature radii for waveguides close to a side surface of the optical waveguide block are omitted. The predefined distance may be larger than one quarter and smaller than three quarters of the radial extension of the optical waveguide block at the coupling end, in particular half of the radial extension of the optical waveguide block at the coupling end.

The longitudinal axis of the optical fiber element is in this case considered to extend into the optical waveguide block to form a reference axis for the optical waveguide block. The longitudinal axis of the optical waveguide block does not necessarily coincide with the longitudinal axis of the optical fiber element. If the optical waveguide block is rotationally symmetric, the rotational axis of symmetry may coincide with the longitudinal axis of the optical fiber element. In other words, the rotational axis of symmetry of the optical waveguide block may line up with the longitudinal axis of the optical fiber element. In this case, the rotational axis of symmetry of the optical waveguide block may be similarly used as reference axis.

As used herein, a "lateral part" of the object end refers to a surface area of the optical waveguide block facing in a direction inclined to the reference axis of the optical waveguide block (corresponding, for instance, to the extension of the longitudinal axis of the optical fiber element) at an angle of more than or equal to 45° and less than or equal to 135°. Correspondingly, a "forward facing part" of the object end refers to a surface area of the optical waveguide block facing in a direction inclined to the reference axis of the optical waveguide block at an angle of less than 45° and a "backward facing part" of the object end refers to a surface area of the optical waveguide block facing in a direction inclined to the reference axis of the optical waveguide block at an angle of more than 135°. For these considerations, the reference axis is considered to have a direction facing away from the distal end of the optical fiber element. Thus, the "forward facing part" of the object end faces away from the distal end of the optical fiber element. The respective angles may be measured between the surface normal of the respective surface area and the reference axis. The surface normal may be considered to have a direction facing away from the optical waveguide block.

The optical waveguide block may be covered at least partially by an electrically conductive layer. The electrically conductive layer may be electrically coupled to a further conductor extending to the proximal end of the optical endoscope. Via this conductor and the conductive layer of the optical waveguide block, it is possible to transmit current to the distal end for ablation purposes.

The electrically conductive layer covering the optical waveguide block may particularly be transparent or semi-transparent at the operating wavelength of the optical endoscope. For that purpose, the electrically conductive layer may be formed of a transparent or semi-transparent material and/or the electrically conductive layer may have a thickness allowing a predefined fraction of light at the operating wavelength of the optical endoscope to pass through the layer without being scattered. The predefined fraction may be 50% or more.

Possible materials for the electrically conductive layer include wide band gap semiconductor materials, such as indium tin oxide or aluminum doped zinc oxide, ultrathin metals, silver nanowires and/or metal grids. For example, ultrathin metals and metal grids may be combined to achieve high optical transmission for wavelengths above 1 μm while still maintaining low electrical resistance (high conductance). For medical applications the material or at least the outer surface of the electrically conductive layer needs to be compatible with human tissues. For such applications, gold may be used as material for the electrically conductive layer or its outer surface. The outer surface refers to the surface of the electrically conductive layer that may come into contact with human tissues when the optical endoscope is in use.

Alternatively or additionally, the electrically conductive layer may comprise openings for light to enter the two or more optical waveguides. In other words, the openings may form optical ports for the two or more optical waveguides.

If the electrically conductive material covering the optical waveguide block is transparent or semi-transparent at the operating wavelength of the optical endoscope, openings for light to enter the two or more optical waveguides are not necessarily provided. In other words, no such openings or ports may be formed in this case. Thus, the manufacturing may be simplified.

The invention further provides an optical waveguide block for an optical endoscope, the optical waveguide block comprising a rigid material, wherein two or more optical waveguides are formed in the rigid material. The optical waveguide block may comprise any one or more of the above-described features.

The invention further provides a method for manufacturing an optical endoscope comprising the steps of:
  providing an optical fiber element with a proximal end and a distal end,
  providing an optical waveguide block comprising a rigid material,
  forming two or more optical waveguides in the rigid material, and
  connecting the optical waveguide block to the distal end of the optical fiber element.

The two or more optical waveguides may particularly be formed by ultrafast laser inscription.

The optical endoscope, particularly the optical waveguide block, may comprise any one or more of the above-described features.

Advantageous embodiments will now be described in combination with the enclosed Figures.

DETAILED DESCRIPTION

Figure 1:
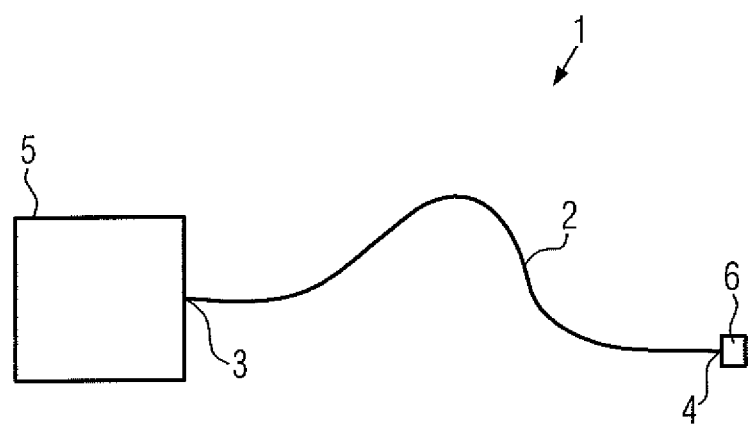
FIG. 1 illustrates the basic setup of an optical endoscope according to the invention in a schematic illustration.

FIG. 1 illustrates in a schematic way the basic setup of an optical endoscope according to the invention. The optical endoscope 1 comprises an optical fiber element 2, typically including one or more optical fibers arranged within a flexible sheath material. The optical fiber element 2 has a proximal end 3 and a distal end 4. At the proximal end 3 imaging optics element 5 is arranged. The imaging optics element 5 may comprise optics for imaging the light transmitted via the optical fiber element 2 onto, for instance, a digital image sensor. The imaging optics element 5 may also comprise an LCD display to display the image obtained from the digital image sensor. The elements provided at the proximal end 3 of the optical fiber element 2 are standard elements known per se.

At the distal end 4 of the optical fiber element 2, an optical waveguide block 6 is arranged. As further detailed below, the optical waveguide block 6 comprises a rigid material in which two or more optical waveguides are formed. This optical waveguide block 6 allows providing an improved optical endoscope 1 as will also become apparent from the specific embodiments described herein below.

The optical fiber element 2 extends along a longitudinal direction, which defines the longitudinal axis of the optical endoscope 1. Since the optical fiber element 2 is usually flexible, the longitudinal direction/axis will normally be curved. The optical fiber element 2 is usually cylindrical with the central axis defining the symmetry axis of the cylinder. The longitudinal axis of the optical fiber element 2 can be considered as extending beyond its proximal and distal ends, in particular as straight lines perpendicular to the proximal/distal end surface. The longitudinal axis of the optical fiber element 2, thus is used herein as a reference axis with regard to which indications such as "lateral" or "radial" should be understood, particularly with respect to the optical waveguide block 6.

Figure 2:
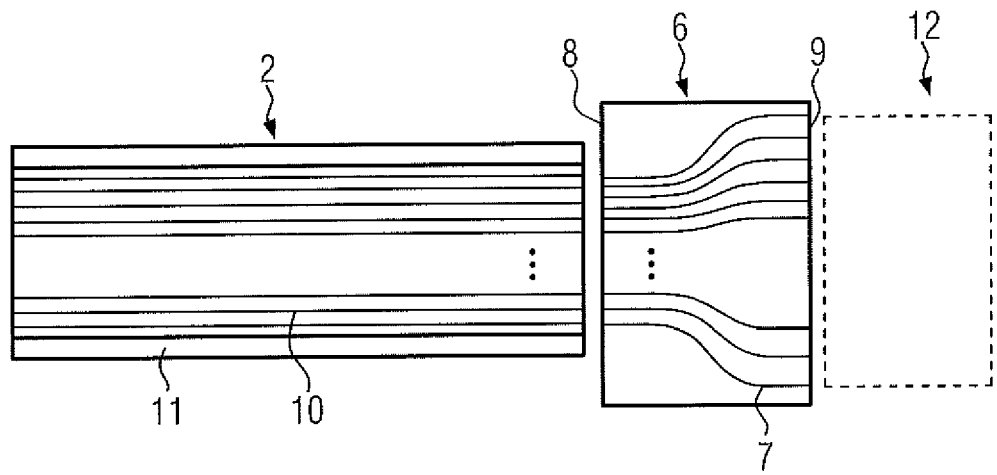
FIG. 2 shows parts of an optical endoscope according to a first embodiment of the invention.

FIG. 2 illustrates a first embodiment of the invention. The optical fiber element 2 comprises a multi-core fiber with a plurality of cores 10 coated in a common, flexible polymer jacket 11. Many different types of multi-core fibers are known. The invention is not particularly limited to any specific embodiment for the multi-core fiber nor to any specific arrangement of the fibers in the optical fiber element 2.

The optical waveguide block 6 has the form of a cuboid in this specific embodiment and is made of glass. The optical waveguide block 6 may also be cylindrical or may have any other desired shape. A cylindrical optical waveguide block 6 would have the same appearance in the cross-sectional view of FIG. 2 as a cuboid one. The invention is not limited to glass as a rigid material for the optical waveguide block 6. The optical waveguide block 6 could also be formed of a rigid polymer or a rigid semiconductor, which are particularly optically transparent at the operating wavelength of the optical endoscope.

The optical waveguide block 6 comprises a plurality of 3-D ultrafast laser inscribed optical waveguides 7 leading from a coupling end 8 of the optical waveguide block 6 to an object end 9. The coupling end 8 faces the optical fiber element 2 while the object end 9 faces the object when the optical endoscope is in use, for instance, the interior of an organ of the human body.

Ultrafast laser inscription is known as such and works as follows: a high-intensity, focused femtosecond laser beam is applied to the rigid material in order to induce a permanent positive refractive index change through a multi-photon absorption mechanism. By 3-D translating the laser focus through the block of rigid material, the path traced out by the focus therefore becomes a light guiding core due to its resultant higher refractive index, with effective cladding provided by the unmodified remainder of the rigid material block. Doing multiple scanning runs enables writing an arbitrary number of waveguides with arbitrary 3-D shapes in a single block of rigid material. Various approaches are possible to account for the fact that the shape of the focused laser is not the ideal shape of a waveguide core, for instance, using multiple scanning runs with a slight offset from each other and annealing the rigid material block after ultrafast laser inscription by heating.

Further details of writing waveguides in glass with a femtosecond laser may be found in K. M. Davis, K. Miura, N. Sugimoto, and K. Hirao, "Writing waveguides in glass with a femtosecond laser", Optics Letters, vol. 21, no. 21, p. 1729, 1996.

In the optical waveguide block 6 of FIG. 2, the object end 9 is a polished flat surface, perpendicular to the longitudinal axis of the optical fiber element 2. In view of the coupling between the optical waveguide block 6 and the optical fiber element 2, the longitudinal axis of the optical fiber element 2 may be considered as extending into the optical waveguide block 6, with the object end 9 being perpendicular thereto. It is also possible to arrange the object end 9 at a slight angle with regard to the longitudinal axis to remove or minimize back reflections. The angle depends on the refractive indices of the block and the surrounding medium. Typically it varies between a few degrees and ten degrees. The angle, thus, may be more than 1° and less than 10°.

In general, the coupling end 8 is defined by the surface of the optical waveguide block 6 where the ends of the optical waveguides 7 are arranged facing the optical fiber element 2, while the object end 9 is defined as the surface area of the optical waveguide block 6 in which the ends of the optical waveguides 7 are arranged facing the object when the optical endoscope is in use or in other words, facing away from the optical fiber element 2.

In the embodiment of FIG. 2, the optical waveguides 7 in the optical waveguide block 6 fan out from the coupling end 8 towards the object end 9, effectively replicating the distribution of the waveguide ends at the coupling end 8, just with a larger inter-core spacing. The field of view is thus increased. The field of view is increased at the expense of spatial resolution; however, the acceptance angle remains the same as in a regular multi-core fiber endoscope.

Every core 10 of the multi-core fiber of the optical fiber element 2 butt-couples in this example to an end of an optical waveguide 7 at the coupling end 8 (not illustrated in the Figure). In this way, transmission of light from the object end 9 to the proximal end of the optical endoscope is possible.

Optionally, at least one additional optical element 12, such as a GRIN rod lens or micro lens or multiple such lenses, may be attached at the object end 9. If only using single mode waveguides, this embodiment is also compatible with coherent imaging techniques such as optical coherence tomography.

The object end pattern of the optical waveguides 7 is not particularly limited. The distribution could also be monodimensional, i.e. a linear array of waveguides or otherwise different from the distribution of the ends of the waveguide 7 at the coupling end 8. Similarly, the coupling end pattern may be one-dimensional or two-dimensional.

The fully rigid construction of the optical waveguide block 6 ensures long-term stability and no degradation in optical signal.

Figure 3:
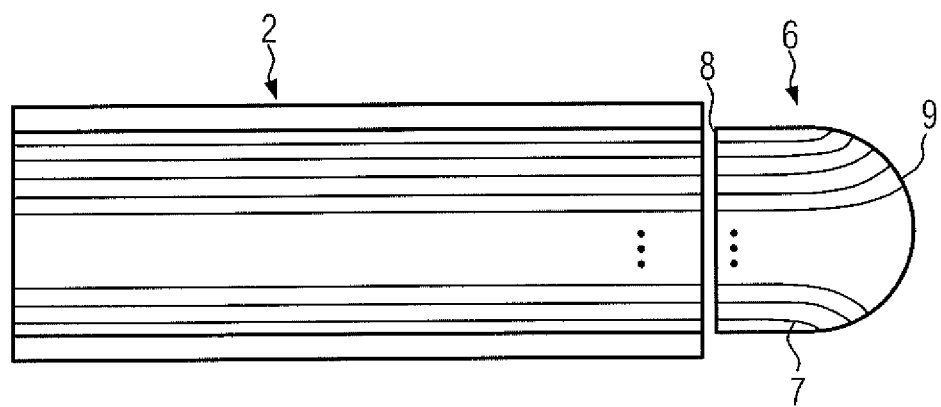
FIG. 3 shows parts of an optical endoscope according to a second embodiment of the invention.

FIG. 3 illustrates another embodiment of the invention. In contrast to the embodiment of FIG. 2, the optical waveguide block 6 has an object end 9 that is hemispherical. Optical waveguides 7 in the optical waveguide block 6, thus, map the flat 2-D distribution of the coupling end 8 to the 3-D hemisphere, thereby increasing the solid angle. In other words, optical waveguides 7 also lead to a side surface of the optical waveguide block 6 with respect to the longitudinal axis of the optical fiber element 2 as reference axis. In this way, the solid angle may be increased to $2\pi$. The maximum solid angle can be even larger in the case of the optical waveguides 7 bending backwards. This may introduce, however, optical loss, since waveguide losses increase as the waveguide radius decreases.

Figure 4:
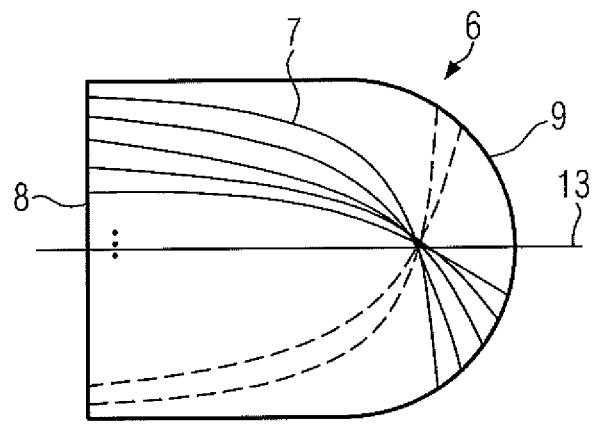
FIG. 4 shows an exemplary optical waveguide block for an optical endoscope according to the invention.
Figure 5:
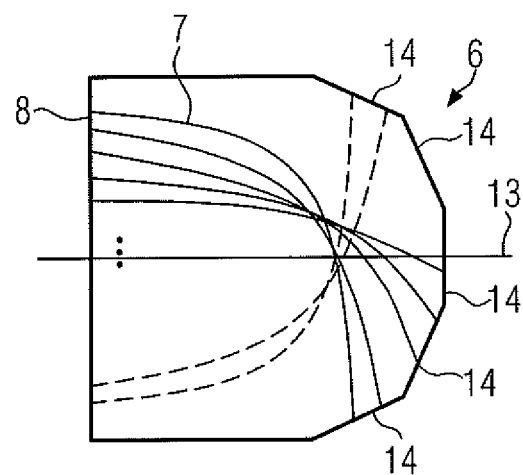
FIG. 5 shows another exemplary optical waveguide block for an optical endoscope according to the invention.

FIGS. 4 and 5 illustrate possible alternatives to the optical waveguide block 6 illustrated in FIG. 3. In FIGS. 4 and 5, a theoretical plane 13 extending parallel to the longitudinal axis of the optical fiber element 2 and including the symmetry axis of the optical fiber element 2 is illustrated. In some embodiments, instead of plane 13, the rotational axis of symmetry of the optical waveguide block 6 may be used as reference. Waveguides 7 lead from one lateral side of the plane or axis 13 at the coupling end 8 to the other lateral side of the plane or axis 13 on the object end 9. In this way, it is possible to maintain the radius of curvature large enough to keep curvature losses acceptably low. The optical waveguides 7 may be designed with angles and distances from each other in such a manner to minimize crosstalk (see FIG. 5). In both alternatives (FIG. 4 and FIG. 5) the optical waveguides 7 are not intersecting in three-dimension, but only in projection.

FIG. 5 further shows the alternative of composing the object end 9 of a plurality of flat facets 14, which together join in a prismatic manner to cover the hemispherical object end 9. This discontinuous design of the hemispherical object end 9 may be used independently of the optical waveguide pattern inside the optical waveguide block 6.

Figure 6:
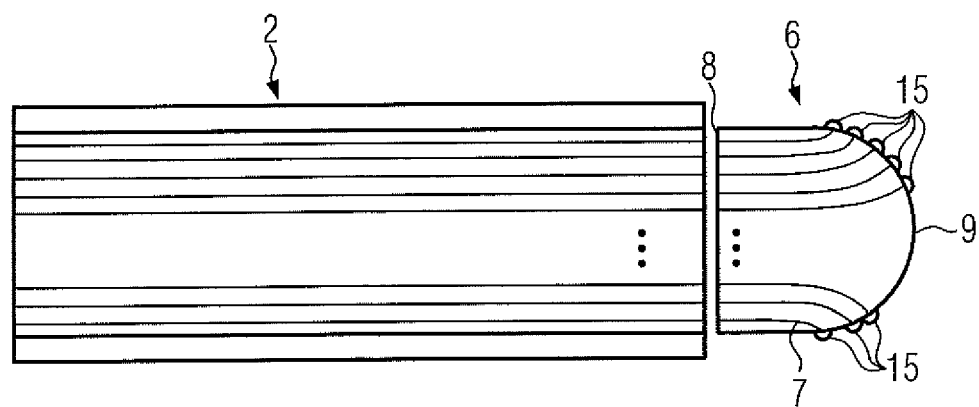
FIG. 6 shows parts of an optical endoscope according to a third embodiment of the invention.

FIG. 6 illustrates a further embodiment of the invention, which basically corresponds to the embodiment described with reference to FIG. 3. In this case, however, micro lenses 15 are affixed to the optical waveguide ends at the object end 9 of the optical waveguide block 6. In particular, microscopic plano-convex lenses 15 made from fused silica or silicon are used in this example. In this embodiment, a hemispherical object space is imaged and transmitted through the optical fiber element 2 towards the proximal end. In the case of all waveguides being single mode, optical coherence tomography may be used, as mentioned above, with the number of pixels equal to the number of waveguides in the optical waveguide block 6.

Figure 7:
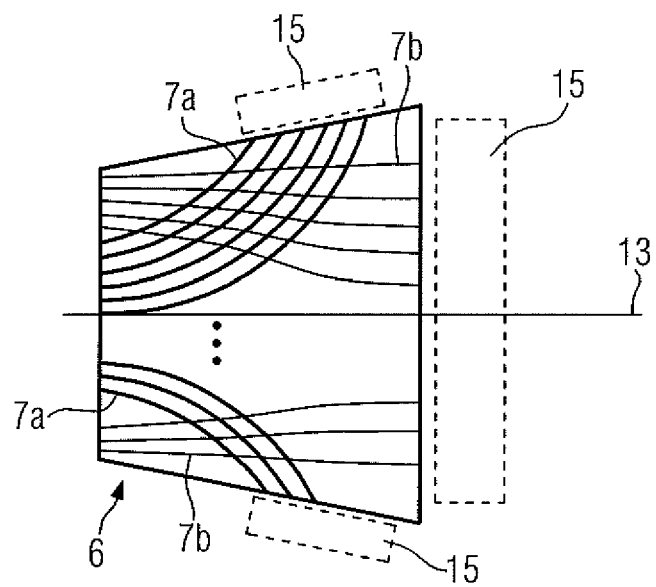
FIG. 7 shows another exemplary optical waveguide block for an optical endoscope according to the invention.

FIG. 7 illustrates an alternative optical waveguide block 6, which may be used to reduce curvature loss. In this example, optical waveguides 7a closer to the plane or axis 13 are mapped to the lateral surface areas of the object end, while the optical waveguides 7b closer to the edge of the optical waveguide block 6 map to a forward facing surface area of the object end. The side facing surface area can either be a cylindrical surface, or through the use of micro lenses with different focal lengths can be modified to more closely match a hemispherical surface. Likewise, the forward facing surface area can be flat as illustrated in FIG. 2 or curved as illustrated, for instance, in FIG. 3.

Optional micro lenses or GRIN optics are illustrated as additional optical elements 15 in FIG. 7.

Figure 8:
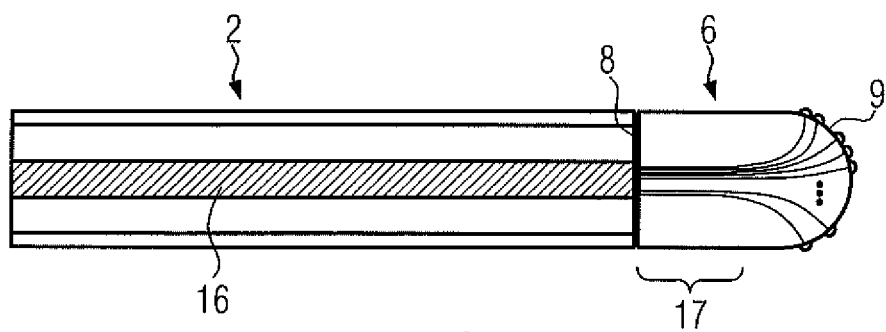
FIG. 8 shows parts of an optical endoscope according to a fourth embodiment of the invention.

FIG. 8 illustrates another embodiment of the invention, which uses instead of a multi-core fiber for the optical fiber element 2 a multi-mode fiber 16. All the previous embodiments discussed herein can also be used with a multi-mode fiber. Coherent imaging techniques, such as optical coherence tomography, however, cannot be implemented with a multi-mode fiber. In order to couple the two or more optical waveguides in the optical waveguide block 6 to the multi-mode fiber 16 a photonic lantern section 17 is provided, which is also obtained by ultrafast laser inscription.

Figure 9A:
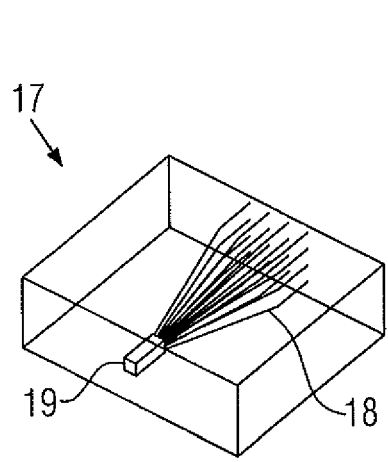
FIGS. 9a and 9b illustrate a photonic lantern usable in the context of an optical endoscope according to the invention.
Figure 9B:
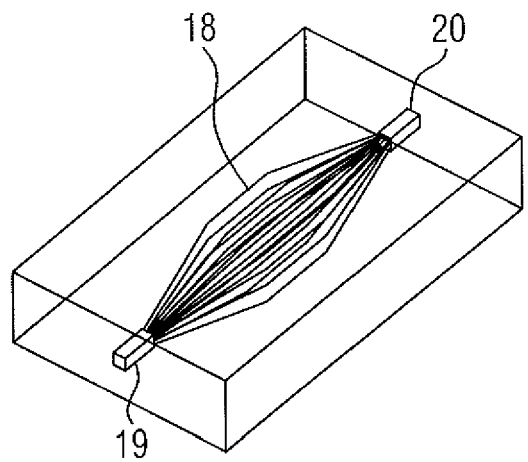

FIGS. 9a and 9b illustrate so-called "photonic lanterns". Photonic lanterns are optical devices connecting a multi-mode waveguide to a plurality of waveguides with fewer, possibly only single, modes. FIG. 9a shows the alternative of mapping one multi-mode waveguide 19 to a number of single mode waveguides 18. FIG. 9b illustrates spreading out of a multi-mode waveguide 19 to a plurality of single mode waveguides 18 and then recombining to a single multi-mode waveguide 20 again. This alternative is particularly useful, since FBG (Fiber Bragg Grating) filters can be inscribed in the region of the single mode waveguides 18. From the alternative shown in FIG. 9b, the photonic lantern takes its name. Both embodiments of the photonic lanterns shown in FIGS. 9a and 9b may be used in the context of the present invention. FBG (Fiber Bragg Grating) filters may be inscribed in the optical waveguide block 6, particularly in the single mode waveguides 18 of a photonic lantern section 17.

Referring again to FIG. 8, the modes of the multi-mode fiber 16 first couple to the individual waveguides in the photonic lantern section 17 and then spread out according to the needs of the specific embodiment. In this case, the object end 8 is made consistent with the example shown in FIG. 6.

Since endoscopes using a multi-mode fiber are sensitive to bending during use, it is necessary to obtain a transfer function for effective operation, as known per se in the art.

Figure 10:
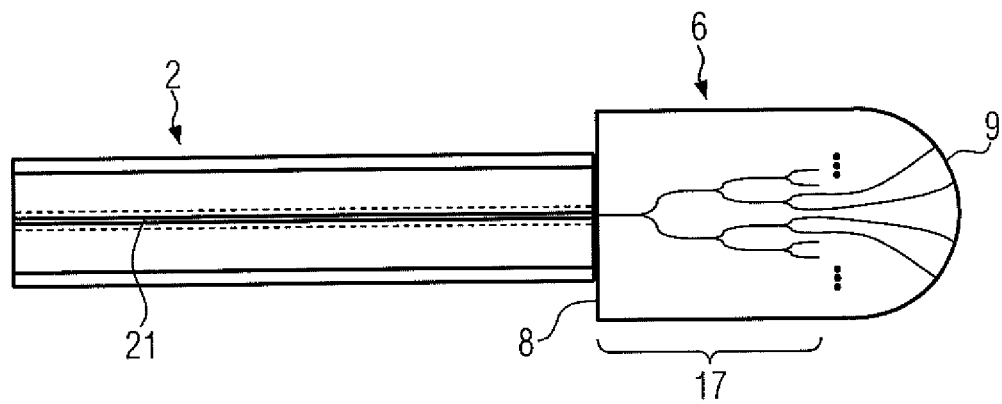
FIG. 10 shows parts of an optical endoscope according to a fifth embodiment of the invention.

FIG. 10 shows another embodiment of an optical endoscope according to the invention. For the optical fiber element 2, a single mode or multi-mode fiber 21 may be used. Again a photonic lantern section 17 is written into the optical waveguide block 6. The optical lantern section 17 is implemented in a branched manner, that is, with a spread out from a multi-mode waveguide to fewer-moded waveguides occurring over multiple fan out steps.

If a multi-mode fiber is used for the optical fiber element 2, at every splitting level, the number of modes from the larger input waveguide is divided up amongst its branches. Functionally, this alternative is identical to the embodiment described with reference to FIG. 8 with the only difference being that the photonic lantern section 17 does not fan out at once.

According to the alternative of a single mode fiber being used for the optical fiber element 2, each branch functions as a splitter rather than a fan out device. In this manner, it is possible for the single mode input light propagating toward the object end 9 to split and coherently reach the entire field of view. The photonic lantern section 17, thus, functions as the multiplexing element.

Figure 11:
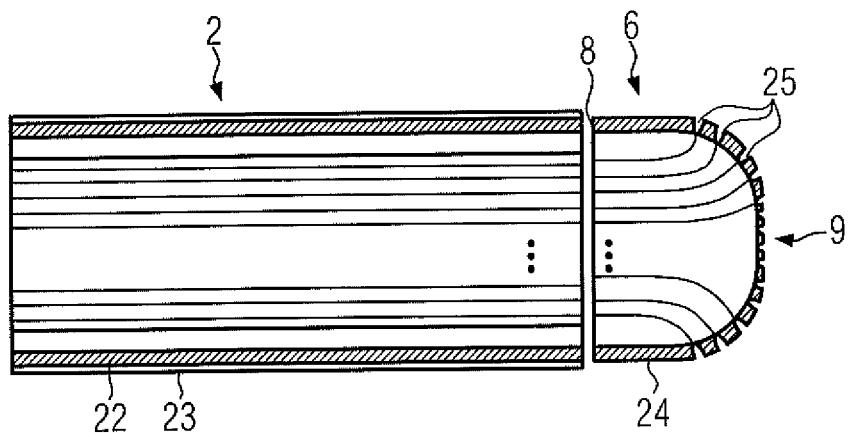
FIG. 11 shows parts of an optical endoscope according to a sixth embodiment of the invention.

Another embodiment of the invention is illustrated with reference to FIG. 11. Sometimes, optical endoscopes are intended to be used for radiofrequency ablation of internal tissues. The embodiment of FIG. 11 is suitable for such purposes. Particularly, a conductive tube 22 of a conductive material, such as a metal, is provided around optical fiber element 2 with an optional insulating sheath 23. The optical waveguide block 6 is embedded in a conductive layer 24, which has proper openings 25 for optical access to the optical waveguides of the optical waveguide block 6. Current may be transmitted to the distal end by means of the conductive tube 22 surrounding the optical fiber element 2. Optionally, several layers of conductive and insulating tubes may surround the optical fiber element 2 to enable ring electrodes for monitoring purposes. The conductive tube 22 is in electrical contact with the conductive layer 24 of the optical waveguide block 6, so that the current may be transmitted to the conductive layer 24 of the optical waveguide block 6. In this way, ablation treatments can be performed. This radiofrequency ablation functionality can be used with any one of the previous embodiments. If a multi-mode fiber should be used for the optical fiber element 2, a photonic lantern section as illustrated in FIG. 8 or 10 can be inscribed in the optical waveguide block.

In an alternative embodiment, the conductive layer 24 may be semi-transparent or transparent at the operating wavelength of the optical endoscope. In this case, the openings 25 may be omitted. The conductive layer 24 may particularly be formed of a transparent or semi-transparent material and/or may be made sufficiently thin to allow light at the operating wavelength of the optical endoscope to pass at least partially through the layer.

Figure 12:
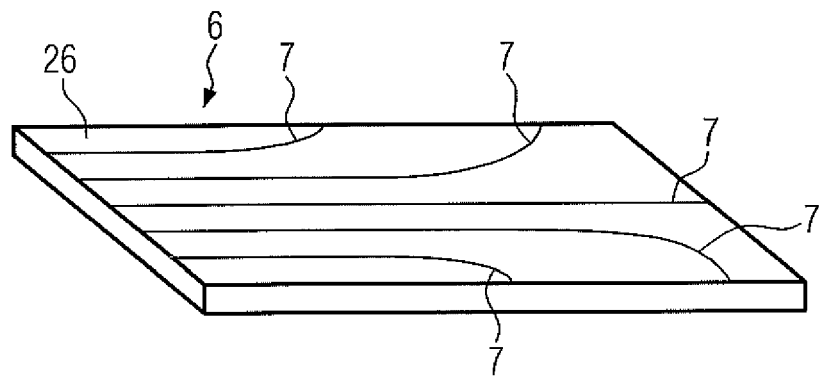
FIG. 12 shows another exemplary optical waveguide block for an optical endoscope according to the invention.
Figure 13:
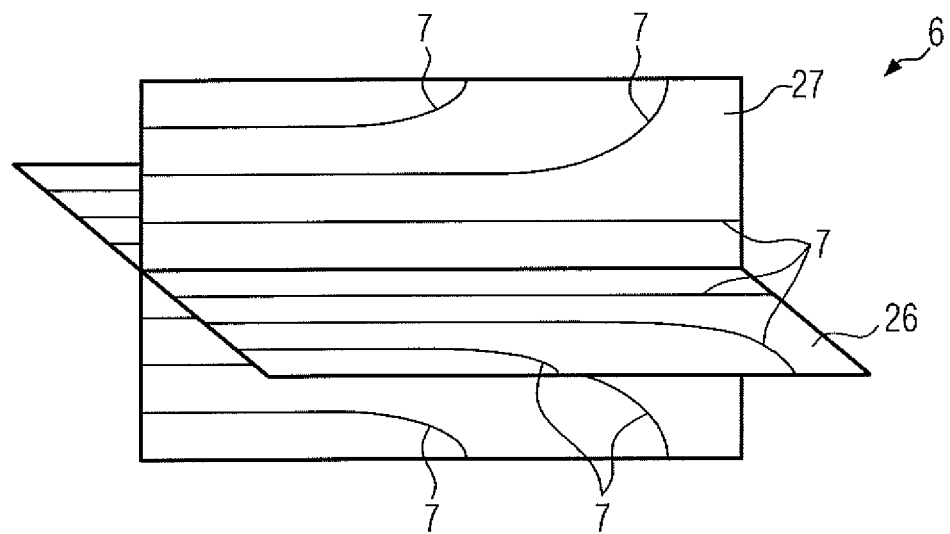
FIG. 13 shows another exemplary optical waveguide block for an optical endoscope according to the invention.

FIGS. 12 and 13 illustrate further alternatives for the optical waveguide block 6, as it may be used for optical endoscopes according to the invention.

In FIG. 12, the optical waveguide block 6 is formed as a planar chip 26 with a 2-D distribution of five exemplary optical waveguides 7 formed therein. The central optical waveguide extends straight or uncurved from the coupling end to the object end, while the other optical waveguides are curved towards a side surface of the planar chip 26. The thickness of the planar chip 26 is significantly less than its length and width.

In FIG. 13, the optical waveguide block 6 is formed by two orthogonally intersecting planar chips 26, 27 each with a 2-D distribution of optical waveguides 7 formed therein. The planar chips 26, 27 are arranged such that each of planar chips 26, 27 is divided in half by the respective other chip. In this way, a 3-D distribution of the optical waveguides 7 may be achieved while reducing the amount of rigid material. Each of the planar chips 26, 27 may comprise two or more elements. For instance, the planar chip 26 may comprise two halves, each connected to the planar chip 27.

In the described embodiments, the optical waveguides formed in the rigid material of the optical waveguide block 6 may be single-mode or multi-mode waveguides.

Although the previously discussed embodiments and examples of the present invention have been described separately, it is to be understood that some or all of the above-described features can also be combined in different ways. For instance, the described optical waveguide blocks may be used in combination with different kinds of optical fiber elements.

In the figures, several features are only illustrated in a schematic way. For instance, the optical waveguide block is often shown as spaced from the distal end of the optical fiber element, This is only for illustrational purposes. The optical waveguide block is actually coupled with the distal end of the optical fiber element such that light may be transmitted via the two or more optical waveguides and the optical fiber element to the proximal end of the endoscope. For instance, a butt coupling may be realized.

The discussed embodiments are not intended as limitations, but serve as examples illustrating features and advantages of the invention. Particularly, the pattern of the optical waveguides in the optical waveguide block is determined by the desired application. Similarly, while glass is used for the optical waveguide block according to the embodiments, the optical waveguide block may consist of any transparent, rigid material of appropriate index of refraction that offers the possibility of hosting 3-D optical waveguides as described. With the described embodiments, it is possible to increase the field of view or the solid angle over known optical endoscopes. This is possible while at the same time providing a mechanically reliable, inexpensive solution that can be used with any type of fiber.

The invention claimed is:

1. An optical endoscope comprising:
   an optical fiber element comprising:
      a proximal end; and
      a distal end, and
   an optical waveguide block arranged at the distal end of the optical fiber element, the optical waveguide block comprising a rigid material with two or more optical waveguides formed therein, each of the two or more optical waveguides comprising:
      a coupling end facing the optical fiber element and arranged on a first surface of the optical waveguide block; and
      an object end facing away from the optical fiber element and arranged on a second surface of the optical waveguide block,
      wherein a mapping of a spatial distribution of the coupling ends of the two or more optical waveguides to a spatial distribution of the object ends of the two or more waveguides is mirror symmetrical with regard to a plane extending parallel to a longitudinal axis of the optical fiber element.

2. The optical endoscope of claim 1, wherein the two or more optical waveguides are integrally formed with the rigid material of the optical waveguide block.

3. The optical endoscope of claim 1, wherein the two or more optical waveguides are formed by parts of the rigid material having a higher refractive index than their surrounding parts.

4. The optical endoscope of claim 1, wherein the two or more optical waveguides are obtained by ultrafast laser inscription.

5. The optical endoscope of claim 1, wherein the rigid material is optically transparent at an operating wavelength of the optical endoscope.

6. The optical endoscope of claim 1, wherein the rigid material comprises a glass, a polymer and/or a semiconductor.

7. The optical endoscope of claim 1, wherein the optical fiber element comprises a multi-core optical fiber and wherein the two or more optical waveguides are coupled to the optical fiber element such that at the coupling end the two or more optical waveguides line up with cores of the multi-core optical fiber.

8. The optical endoscope of claim 7, wherein the cores of the multi-core optical fiber are single mode cores.

9. The optical endoscope of claim 1, wherein the optical fiber element comprises a multi-mode optical fiber and wherein the two or more optical waveguides are coupled to the multi-mode optical fiber via a photonic lantern section formed in the rigid material of the optical waveguide block.

10. The optical endoscope of claim 1, wherein the object end is a flat surface perpendicular to or inclined with regard to the longitudinal axis of the optical fiber element.

11. The optical endoscope of claim 10, wherein the two or more optical waveguides fan out from the coupling end to the object end such that an inter-core spacing at the object end is larger than at the coupling end.

12. The optical endoscope of claim 1, wherein the object end is hemispherical.

13. The optical endoscope of claim 1, wherein additional optics comprising one or more GRIN lenses and/or one or more micro lenses are coupled with the optical waveguide block.

14. The optical endoscope of claim 1, wherein the optical waveguide block is covered at least partially by an electrically conductive layer, wherein the electrically conductive layer is transparent or semi-transparent at an operating wavelength of the optical endoscope.

15. The optical endoscope of claim 1, wherein the optical waveguide block comprises one or more planar chips.

16. The optical endoscope of claim 1, wherein the optical waveguide block is formed by two orthogonally intersecting planar chips in a three-dimensional arrangement.

17. The optical endoscope of claim 1,
wherein the optical waveguide block comprises a rounded object end facing away from the optical fiber element.

* * * * *